United States Patent [19]

Shirafuji et al.

[11] Patent Number: 5,237,075
[45] Date of Patent: Aug. 17, 1993

[54] PROCESS FOR PRODUCING 3,4-DIHYDROCOUMARIN DERIVATIVES

[75] Inventors: Tamio Shirafuji; Kiyomi Sakai; Kensen Okusako; Itaru Kawata, all of Ehime; Yasumoto Simazu, Osaka; Tetuya Suzuta, Hyogo, all of Japan

[73] Assignee: Sumitomo Chemical Co., Ltd., Osaka, Japan

[21] Appl. No.: 839,285

[22] Filed: Feb. 24, 1992

Related U.S. Application Data

[63] Continuation of Ser. No. 587,877, Sep. 25, 1990, abandoned.

[30] Foreign Application Priority Data

Sep. 25, 1989 [JP] Japan .................................. 1-249748
Sep. 25, 1989 [JP] Japan .................................. 1-249749

[51] Int. Cl.$^5$ ........................................ C07D 311/10
[52] U.S. Cl. ........................................ 549/290
[58] Field of Search ........................................ 549/290

[56] References Cited

U.S. PATENT DOCUMENTS 3,442,910 5/1969 Thweatt et al. ........................ 549/290
4,772,728 9/1988 Korte et al. ........................... 549/290

OTHER PUBLICATIONS

J. Am. Chem. Soc., vol. 62, pp. 283–287 (1940).
J. Am. Chem. Soc., vol. 62, pp. 3067–3070 (1940).
Chemical Abstracts, vol. 104, No. 11, p. 647, Abstract No. 88436w, Matsuda (Mar, 17, 1986).
Griffiths et al, Synthetic and Stereochemical Studies of the Octahydro-1-benzopyran System, J. Chem. Soc. Perkin Trans. II, pp. 431–436 (1988).

Primary Examiner—Jane T. Fan
Attorney, Agent, or Firm—Sughrue, Mion, Zinn, Macpeak & Seas

[57] ABSTRACT

A process for producing a 3,4-dihydrocoumarin compound represented by formula (II):

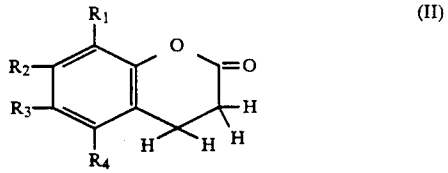

wherein $R_1$ to $R_4$ are as defined in the specification, comprising the steps of:
(1) heating a 3-(2-cyclohexanoyl)propionic acid ester compound represented by formula (I):

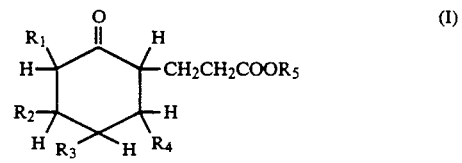

wherein $R_1$ $R_5$ are as defined in the specification, in the presence of at least one solid metal catalyst, thereby to allow said compound of formula (I) to undergo ring formation and dehydrogenation to yield said 3,4-dihydrocoumarin compound of formula (II) and, as a by-product, a coumarin compound represented by formula (III):

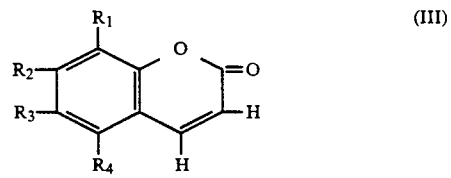

wherein $R_1$ to $R_4$ are as defined above;
(2) adding a catalyst which is as defined above to said reaction mixture, or bringing said reaction mixture into contact with oxygen to activate said catalyst used in said ring formation and dehydrogenation, without separating said coumarin compound from the reaction mixture that has undergone said ring formation and dehydrogenation; and
(3) partially hydrogenating said by-product coumarin compound in said reaction mixture with hydrogen so as to convert said coumarin compound to a 3,4-dihydrocoumarin compound.

10 Claims, No Drawings

PROCESS FOR PRODUCING 3,4-DIHYDROCOUMARIN DERIVATIVES

This is a continuation of application Ser. No. 07/587,877 filed Sep. 25, 1990 now abandoned.

FIELD OF THE INVENTION

The present invention relates to an improvement in a process for the preparation of a 3,4-dihydrocoumarin derivative from a 3-(2-cyclohexanoyl)propionic acid ester derivative.

3,4-Dihydrocoumarin derivatives are important compounds, e.g., in the perfume industry.

BACKGROUND OF THE INVENTION

In a conventionally employed method for producing a 3,4-dihydrocoumarin derivative, a 3-(2-cyclohexanoyl)-propionic acid ester derivative is heated in the presence of a hydrogenation-dehydrogenation catalyst such as palladium to perform ring formation and dehydrogenation. In the above reaction, a coumarin derivative is formed as a by-product. This by-product coumarin derivative is separated from the reaction mixture and then partially hydrogenated with hydrogen in the presence of a fresh hydrogenation-dehydrogenation catalyst so as to convert the coumarin derivative into a dihydrocoumarin derivative, and the resulting dihydrocoumarin derivative is recovered (as described, e.g., in U.S. Pat. No. 3,442,910 and J. Am. Chem. Soc., vol. 62, p.p. 283-287 (1940)).

The catalyst for use in the partial hydrogenation reaction may be one obtained by regenerating the catalyst that has been used in the ring formation and dehydrogenation reaction. The regeneration of the catalyst is accomplished by (1) subjecting the catalyst to hydrogen reduction at a high temperature (*Shokubai Sekkei* (Catalyst Design), edited by Shokubai Gakkai, published by Kodansha, Japan) or (2) subjecting the catalyst to cracking at a high temperature (as described, e.g., in U.S. Pat. Nos. 2,506,307 and 2,532,615).

The above-described conventional methods are defective in that both the by-product coumarin derivative and the catalyst should be separated from the reaction mixture, and that it is necessary to conduct the regeneration of the catalyst at a high temperature (about 480° to 600° C.) in either of the above methods (1) and (2). Thus, the separation of the reaction product and the regeneration of the catalyst necessitate troublesome procedures and are uneconomical. In addition, the regeneration method (1) above is dangerous because hydrogen is used at a high temperature.

SUMMARY OF THE INVENTION

The present inventors have conducted intensive studies in order to develop a highly economical process for producing a 3,4-dihydrocoumarin derivative. As a result, it has now been found that if, after a 3-(2-cyclohexanoyl)-propionic acid ester derivative is heated in the presence of a hydrogenation-dehydrogenation catalyst to perform ring formation and dehydrogenation with formation of a coumarin derivative as a by-product, the partial hydrogenation of the by-product coumarin derivative is conducted using hydrogen with the coumarin derivative being kept unseparated from the reaction mixture, the partial hydrogenation reaction proceeds at a higher rate than partial hydrogenation conducted after the coumarin derivative is separated from the reaction mixture.

The present inventors have also found that by bringing the reaction mixture, as it is, that has undergone ring formation and dehydrogenation into contact with oxygen, the catalyst in the reaction mixture is regenerated, and that even if the resulting reaction mixture is then subjected, as it is, to partial hydrogenation using hydrogen, only the by-product coumarin derivative is partially hydrogenated. The present invention has been completed based on these findings.

It is, therefore, an object of the present invention to provide an efficient and economical process for producing a 3,4-dihydrocoumarin derivative.

Other objects and effects of the present invention will be apparent from the following description.

The present invention provides a process for producing a 3,4-dihydrocoumarin derivative represented by formula (II):

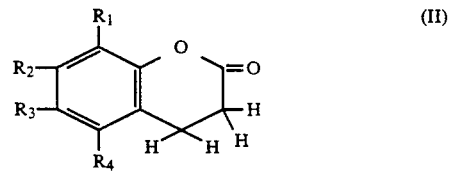

wherein $R_1$ to $R_4$ each represents a hydrogen atom, a methyl group or an ethyl group, provided that at least two of $R_1$ to $R_4$ each represents a hydrogen atom, which process comprises the steps of:

(1) heating a 3-(2-cyclohexanoyl)propionic acid ester derivative represented by formula (I):

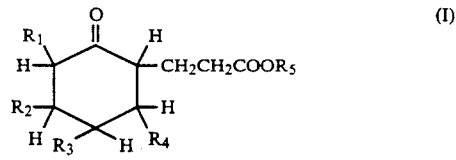

wherein $R_1$ to $R_4$ are as defined above, and $R_5$ represents an alkyl group having 1 to 4 carbon atoms, in the presence of at least one solid metal catalyst selected from the group consisting of platinum, palladium, iridium, rhodium and nickel, thereby to allow the compound of formula (I) to undergo ring formation and dehydrogenation to yield the 3,4-dihydrocoumarin derivative of formula (II) and, as a by-product, a coumarin derivative represented by formula (III):

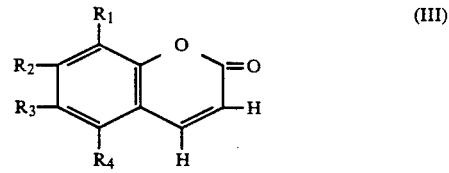

wherein $R_1$ to $R_4$ are as defined above; and (2) partially hydrogenating the coumarin derivative of formula (III), the partial hydrogenation of the by-product coumarin derivative of formula (III) being conducted, while the coumarin derivative is kept unseparated from the reaction mixture that has undergone the ring formation and dehydrogenation, by adding a catalyst which is as defined above to the reaction mixture, or bringing the reaction mixture into contact with oxygen to activate the catalyst used in the ring formation and dehydrogenation; and then bringing the resulting reaction mixture into contact with hydrogen thereby to partially hydrogenate the coumarin derivative of formula (III) so as to convert the coumarin derivative of formula (III) to the 3,4-dihydrocoumarin derivative of formula (II).

DETAILED DESCRIPTION OF THE INVENTION

The 3-(2-cyclohexanoyl)propionic acid ester derivative used in the present invention is represented by formula (I) given above. Examples of this compound include
methyl 3-(2-cyclohexanoyl)propionate,
butyl 3-(2-cyclohexanoyl)propionate,
methyl 3-(3-methyl-2-cyclohexanoyl)propionate,
methyl 3-(5-methyl-2-cyclohexanoyl)propionate,
propyl 3-(4-ethyl-2-cyclohexanoyl)propionate,
ethyl 3-(3,4-dimethyl-2-cyclohexanoyl)propionate,
methyl 3-(3,5-diethyl-2-cyclohexanoyl)propionate,
propyl 3-(3-ethyl-6-methyl-2-cyclohexanoyl)propionate, and the like, but the compound of formula (I) is not limited to these examples. Among the above compounds, methyl 3-(2-cyclohexanoyl)propionate is preferably used.

The catalyst used in the present invention is a heterogeneous catalyst which is at least one member selected from the group consisting of platinum, palladium, iridium, rhodium and nickel. The catalyst is preferably supported on at least one carrier selected from the group consisting of compounds of Group II, III, and IV elements of the periodic table, such as carbon, alumina, silica gel, zeolite, magnesium oxide, barium sulfate, calcium carbonate and the others.

These catalysts may be prepared by known methods, for example, by the impregnation-fixation technique (*Shokubai Jikken Manual* (Catalyst Experiment Manual), edited by Shokubai Gakkai, published by Maki Shoten, Japan) in which a carrier is impregnated with a metal and the resulting carrier is subjected to hydrogen reduction at a high temperature. However, a commercially available catalyst may also be used.

The amount of the catalyst used for the ring formation and dehydrogenation is generally about from 0.1 to 5% by weight, preferably about from 0.5 to 2% by weight, based on the amount of the 3-(2-cyclohexanoyl)propionic acid ester derivative, because too small an amount of the catalyst results in a low reaction rate, whereas too large an amount thereof is costly although the reaction rate is high.

The ring formation and dehydrogenation reaction of the 3-(2-cyclohexanoyl)propionic acid ester derivative may be carried out generally at about from 100° to 350° C., preferably at about from 230° to 260° C. Temperatures outside the above range are not preferred because too low a temperature results in a low reaction rate, while a temperature exceeding about 350° C. tends to cause the starting material and/or the product to decompose.

The ring formation and dehydrogenation reaction may be conducted by using a solvent. Examples of the solvent include phenyl ether, benzyl ether, methyl α-naphthyl ether, ethylnaphthalene, dimethylbiphenyl, dodecane, tetradecane, tetralin, acetophenone, phenyl propyl ketone, methyl benzoate, dimethyl glutamate and the like. The amount of the solvent is generally from about 0.5 to about 10 times, preferably from about 1 to about 5 times, the amount of the 3-(2-cyclohexanoyl)propionic acid derivative.

The ring formation and dehydrogenation reaction can be carried out by heating the 3-(2-cyclohexanoyl)propionic acid ester derivative and the catalyst, along with a solvent if required, at a predetermined temperature generally for about 5 to about 45 hours, preferably for about 15 to about 30 hours.

As a result of the reaction, a 3,4-dihydrocoumarin compound and a by-product coumarin derivative are obtained in yields of about from 70 to 80% and about from 3 to 20%, respectively. Besides these compounds, o-ethylphenol, methyl dihydrocinnamate, etc. result as by-products.

After the ring formation and dehydrogenation reaction, the resulting reaction mixture per se can be brought into contact with hydrogen to conduct the partial hydrogenation reaction of the by-product coumarin derivative contained in the reaction mixture. For this reaction, a catalyst is newly added in an amount of generally about from 0.05 to 5% by weight, preferably about from 0.1 to 2% by weight, based on the amount of the 3-(2-cyclohexanoyl)-propionic acid ester derivative used in the ring formation and dehydrogenation reaction.

Alternatively, in place of newly adding a catalyst, the catalyst that has been used for the ring formation and dehydrogenation reaction and is contained in the resulting reaction mixture may be activated and then used to conduct the partial hydrogenation reaction. In order to activate the catalyst, oxygen gas may be bubbled through the reaction mixture at a temperature of about from 0° to 200° C., preferably about from 10° to 150° C., more preferably about from 25° to 85° C., for a period of from about 10 minutes to about 10 hours, preferably from about 30 minutes to about 5 hours, so that the reaction mixture comes into sufficient contact with oxygen. The oxygen gas may be pure oxygen or a mixed gas composed of oxygen and other gas(es), such as air and nitrogen gas containing about 0.5% of oxygen, and the contact may be carried out either at ordinary pressure or at an elevated pressure.

After the activation of the catalyst, the inside of the reactor is replaced with an inert gas such as nitrogen to prepare for partial hydrogenation reaction using hydrogen.

The partial hydrogenation reaction of the by-product coumarin derivative contained in the reaction mixture may be carried out by bringing the reaction mixture, in which a catalyst is newly added or the catalyst has been activated, into contact with hydrogen at a temperature of about from 80° to 160° C., preferably about from 100° to 150° C., at ordinary pressure or an elevated pressure (generally from about 1 to about 10 kg/cm$^2$G, preferably from about 2 to about 5 kg/cm$^2$G) until hydrogen comes to be no longer taken up by the reaction mixture. It is preferred that the reaction mixture is further made in contact with hydrogen for about 10 minutes to about 3 hours, preferably from about 15 minutes to about 2 hours, after hydrogen comes to be no longer taken up by the reaction mixture. This partial hydrogenation reaction proceeds at a high rate as compared with the case in which the by-product coumarin derivative is subjected to partial hydrogenation after being separated from the reaction mixture.

The reaction mixture to be subjected to the partial hydrogenation reaction may contain the solvent that was used for the ring formation and dehydrogenation reaction, or a solvent may be newly added to the reaction mixture for the partial hydrogenation. The amount of the solvent newly added is generally from about 0.5 to about 10 times, preferably from about 1 to about 5 times, the amount of the 3-(2-cyclohexanoyl)propionic acid derivative.

Through this partial hydrogenation, the by-product coumarin derivative can be hydrogenated into 3,4-dihydrocoumarin derivative substantially completely, without changing the 3,4-dihydrocoumarin derivative at all that has been formed by ring formation and dehydrogenation reaction.

After completion of the above reaction, the 3,4-dihydrocoumarin derivative can be easily isolated by ordinary techniques. That is, the compound can be isolated by distillation after separation of the catalyst.

As described above, the process of the present invention needs no troublesome procedures and is able to produce a 3,4-dihydrocoumarin derivative efficiently at high reaction rates.

The present invention will be explained in more detail by reference to the following examples, which should not be construed to be limiting the scope of the invention. Unless otherwise indicated, all parts, percents, etc. are by weight.

EXAMPLE 1

300 Grams of methyl 3-(2-cyclohexanoyl)propionate was mixed with 1.5 g of a catalyst consisting of active carbon and 5% by weight of palladium supported thereon. This mixture was placed in an autoclave, which was then replaced with nitrogen. The mixture in the autoclave was then heated at 250° C. for 23 hours with stirring at 300 rpm.

The resulting reaction mixture was analyzed by gas chromatography, and it was found that the conversion of the methyl 3-(2-cyclohexanoyl]propionate was 99.8% and the yields of 3,4-dihydrocoumarin and coumarin were 69% and 5%, respectively.

Thereafter, 0.3 g of a catalyst consisting of active carbon and 5% by weight of palladium supported thereon was added to the reaction mixture (the amount of the catalyst being 0.1% by weight based on the amount of the starting methyl 3-(2-cyclohexanoyl)propionate used). The temperature of the resulting reaction mixture in the autoclave was adjusted to 120° C., and partial hydrogenation reaction was carried out with stirring at 800 rpm while the inside of the autoclave was maintained at 2 kg/cm² with hydrogen. The time required to complete the partial hydrogenation reaction (the time required for hydrogen to come to be no longer absorbed) was 50 minutes. This 50-minute period include a 20-minute period (hereinafter, referred to as an aging period) during which the reaction was allowed to further proceed after hydrogen absorption came to no longer take place.

As a result, the yield of 3,4-dihydrocoumarin formed by the partial hydrogenation reaction was 99% based on the coumarin, and the overall yield of the product based on the methyl 3-(2-cyclohexanoyl)propionate was 74%.

COMPARATIVE EXAMPLE 1

In an autoclave were placed 210 g of 3,4-dihydrocoumarin and 15 g of coumarin both isolated from a reaction mixture. Thereto was added 0.3 g of a catalyst consisting of active carbon and 5% by weight of palladium supported on the active carbon. The resulting mixture in the autoclave was kept at 120° C., and partial hydrogenation reaction was carried out with stirring at 800 rpm while the inside of the autoclave was maintained at 2 kg/cm² with hydrogen. The time required to complete the partial hydrogenation reaction was 4 hours (including a 20-minute aging period).

The yield of 3,4-dihydrocoumarin formed by the partial hydrogenation reaction was 87% based on the coumarin.

EXAMPLE 2

300 Grams of methyl 3-(2-cyclohexanoyl)propionate was mixed with 1.5 g of a catalyst consisting of active carbon and 5% by weight of palladium supported thereon. This mixture was placed in an autoclave, which was then replaced with nitrogen. The mixture in the autoclave was then heated at 250° C. for 23 hours with stirring at 300 rpm.

The resulting reaction mixture was analyzed by gas chromatography, and it was found that the conversion of the methyl 3-(2-cyclohexanoyl)propionate was 99.9% and the yields of 3,4-dihydrocoumarin and coumarin were 70% and 5%, respectively. Besides these compounds, methyl dihydrocinnamate and other compounds were found to have been formed as by-products.

The temperature of the reaction mixture was then adjusted to 80° C., and nitrogen gas containing 1% of oxygen was bubbled through the reaction mixture for 30 minutes with stirring at 800 rpm. Thereafter, the inside of the autoclave was replaced with nitrogen gas.

The resulting reaction mixture in the autoclave was heated at 120° C., and partial hydrogenation reaction was carried out with stirring at 800 rpm while the inside of the autoclave was maintained at 2 kg/cm² with hydrogen. The time required to complete the partial hydrogenation reaction was 2 hours (including a 20-minute aging period).

As a result, the yield of 3,4-dihydrocoumarin formed by the partial hydrogenation reaction was 90% based on the coumarin and the overall yield of the product based on the methyl 3-(2-cyclohexanoyl)propionate was 75%.

EXAMPLE 3

The ring formation and dehydrogenation reaction of methyl 3-(2-cyclohexanoyl)propionate was carried out in the same manner as in Example 2. The temperature of the reaction mixture was then adjusted to 80° C., and air was bubbled through the reaction mixture for 30 minutes with stirring at 800 rpm. Partial hydrogenation reaction was then effected in the same manner as in Example 2, and as a result, the time required to complete the partial hydrogenation reaction was 50 minutes (including a 20- minute aging period).

The yield of 3,4-dihydrocoumarin formed by the partial hydrogenation reaction was 95% based on the coumarin.

EXAMPLE 4

The ring formation and dehydrogenation reaction of methyl 3-(2-cyclohexanoyl)propionate was carried out in the same manner as in Example 2. Subsequently, instead of activating the catalyst in the reaction mixture, a catalyst consisting of active carbon and 5% by weight of palladium supported thereon was added to the reaction mixture in an amount of 0.05% by weight based on the amount of the methyl 3-(2-cyclohexanoyl)propionate used. Using the resultant mixture, partial hydrogenation reaction was carried out in the same manner as in Example 2. The time required to complete the partial hydrogenation reaction was 70 minutes (including a 20-minute aging period).

The yield of 3,4-dihydrocoumarin formed by the partial hydrogenation reaction was 93% based on the coumarin.

COMPARATIVE EXAMPLE 2

The ring formation and dehydrogenation reaction of methyl 3-(2-cyclohexanoyl)propionate was carried out in the same manner as in Example 2. The temperature of the reaction mixture was then adjusted to 80° C., and nitrogen gas containing no oxygen was bubbled through the reaction mixture for 30 minutes with stirring at 800 rpm. The resulting reaction mixture was brought into contact with hydrogen in order to conduct partial hydrogenation reaction, but the desired reaction did not proceed at all.

COMPARATIVE EXAMPLE 3

The ring formation and dehydrogenation reaction of methyl 3-(2-cyclohexanoyl)propionate was carried out in the same manner as in Example 2. Without bringing the reaction mixture into contact with oxygen, the resulting reaction mixture was brought into contact with hydrogen in order to conduct partial hydrogenation reaction, but the desired reaction did not proceed at all.

While the invention has been described in detail and with reference to specific embodiments thereof, it will be apparent to one skilled in the art that various changes and modifications can be made therein without departing from the spirit and scope thereof.

What is claimed is:

1. A process for producing a 3,4-dihydrocoumarin compound represented by formula (II):

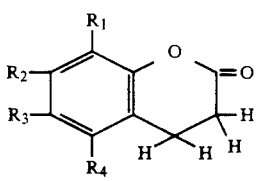

(II)

wherein $R_1$ to $R_4$ each represents a hydrogen atom, a methyl group or an ethyl group, provided that at least two of $R_1$ to $R_4$ each represents a hydrogen atom, said process comprising the steps of:

(1) heating a 3-(2-cyclohexanoyl)propionic acid ester compound represented by formula (I):

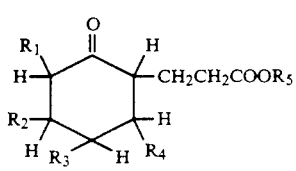

(I)

wherein $R_1$ to $R_4$ are as defined above, and $R_5$ represents an alkyl group having from 1 to 4 carbon atoms, in the presence of at least one solid metal catalyst selected from the group consisting of platinum, palladium, iridium, rhodium and nickel, thereby to allow said compound of formula (I) to undergo ring formation and dehydrogenation at a temperature of about from 230° to 260° C. to yield said 3,4-dihydrocoumarin compound of formula (II) and, as a by-product, a coumarin compound represented by formula (III):

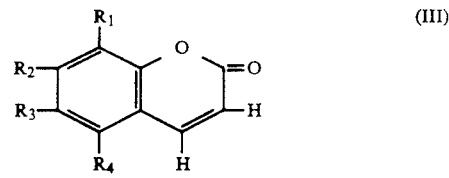

(III)

wherein $R_1$ to $R_4$ are as defined above, in which a 3,4-dihydrocoumarin compound and a by-product coumarin compound are obtained in yields of about from 70 to 80% and about 3 to 20%, respectively;

(2) adding a catalyst which is as defined above to said reaction mixture, or bringing said reaction mixture into contact with oxygen to activate said catalyst used in said ring formation and dehydrogenation, without separating said coumarin compound from the reaction mixture that has undergone said ring formation and dehydrogenation; and (3) partially hydrogenating said by-product coumarin compound in said reaction mixture with hydrogen so as to convert said coumarin compound of formula (III) to 3,4-dihydrocoumarin compound of formula II) at a temperature of about from 80° to 160° C. and at a pressure of about from 1 to 10 kg/cm²G.

2. A process as claimed in claim 1, wherein said 3-(2-cyclohexanoyl)propionic acid ester compound is methyl 3-(2-cyclohexanoyl)propionate.

3. A process as claimed in claim 1, wherein said catalyst is palladium supported on active carbon.

4. A process as claimed in claim 1, wherein the amount of the catalyst used for the ring formation and dehydrogenation is from about 0.1 to about 5% by weight based on the amount of the 3-(2-cyclohexanoyl)-propionic acid ester compound.

5. A process as claimed in claim 1, wherein the amount of the catalyst added for the partial hydrogenation of the by-product coumarin compound is from about 0.05 to about 5% by weight based on the amount of the 3-(2-cyclohexanoyl)propionic acid ester compound.

6. A process as claimed in claim 1, wherein the oxygen which the reaction mixture is brought into contact with is pure oxygen gas or a gas containing oxygen.

7. A process as claimed in claim 1, wherein the contact of the reaction mixture with oxygen is carried out at a temperature of from about 0° C. to about 200° C.

8. A process as claimed in claim 1, wherein the yield of 3,4-dihydrocoumarin formed by the partial hydrogenation reaction is 90% based on the coumarin.

9. A process as claimed in claim 1, wherein the yield of 3,4-dihydrocoumarin formed by the partial hydrogenation reaction is 95% based on the coumarin.

10. A process as claimed in claim 1, wherein the yield of 3,4-dihydrocoumarin formed by the partial hydrogenation reaction is 99% based on the coumarin.

* * * * *